(12) United States Patent
Bammer

(10) Patent No.: US 11,406,300 B2
(45) Date of Patent: Aug. 9, 2022

(54) ASSESSMENT OF FACIAL PARALYSIS AND GAZE DEVIATION

(71) Applicant: iSchemaView, Inc., Menlo Park, CA (US)

(72) Inventor: Roland Bammer, Carlton (AU)

(73) Assignee: iSchemaView, Inc., Menlo Park, CA (US)

( * ) Notice: Subject to any disclaimer, the term of this patent is extended or adjusted under 35 U.S.C. 154(b) by 0 days.

(21) Appl. No.: 17/244,877

(22) Filed: Apr. 29, 2021

(65) Prior Publication Data

US 2021/0338123 A1    Nov. 4, 2021

Related U.S. Application Data

(60) Provisional application No. 63/017,343, filed on Apr. 29, 2020.

(51) Int. Cl.
| A61B 5/16 | (2006.01) |
| A61B 5/00 | (2006.01) |
| G06T 7/11 | (2017.01) |
| G06T 7/00 | (2017.01) |
| A61B 5/02 | (2006.01) |
| A61B 5/055 | (2006.01) |

(52) U.S. Cl.
CPC .......... *A61B 5/163* (2017.08); *A61B 5/02007* (2013.01); *A61B 5/055* (2013.01); *A61B 5/7267* (2013.01); *A61B 5/7475* (2013.01); *G06T 7/0014* (2013.01); *G06T 7/11* (2017.01); *G06T 2207/10081* (2013.01); *G06T 2207/10088* (2013.01); *G06T 2207/20081* (2013.01); *G06T 2207/20084* (2013.01); *G06T 2207/30041* (2013.01)

(58) Field of Classification Search
None
See application file for complete search history.

(56) References Cited

U.S. PATENT DOCUMENTS

| 2010/0318014 A1* | 12/2010 | Latino | A61M 1/32 604/6.14 |
| 2018/0263703 A1 | 9/2018 | Pinter et al. | |
| 2018/0289334 A1 | 10/2018 | De Brouwer et al. | |
| 2019/0027460 A1* | 1/2019 | Fricker | H01L 24/25 |
| 2019/0110754 A1* | 4/2019 | Rao | A61B 5/7275 |
| 2021/0027460 A1* | 1/2021 | Beveridge | G16H 50/20 |
| 2021/0057112 A1* | 2/2021 | Mansi | G16H 80/00 |

FOREIGN PATENT DOCUMENTS

WO    WO-2019144141 A1    7/2019

OTHER PUBLICATIONS

"International Application Serial No. PCT/US2021/030014, International Search Report dated Aug. 24, 2021", 2 pgs.
"International Application Serial No. PCT/US2021/030014, Written Opinion dated Aug. 24, 2021", 6 pgs.

* cited by examiner

*Primary Examiner* — Nancy Bitar
(74) *Attorney, Agent, or Firm* — Schwegman Lundberg & Woessner, P.A.

(57) ABSTRACT

Images of an individual can be obtained and analyzed to determine an amount of facial paralysis of the individual. The images can also be analyzed to determine an amount of gaze deviation of the individual. The amount of facial paralysis of the individual and/or the amount of gaze deviation of the individual can be used to determine a probability that the individual experienced a biological condition.

20 Claims, 9 Drawing Sheets

600

ASSESSMENT OF FACIAL PARALYSIS AND GAZE DEVIATION

PRIORITY CLAIM

This application claims priority to U.S. provisional patent application Ser. No. 63/017,343, filed on Apr. 29, 2020, and entitled "AUTOMATIC ASSESSMENT OF FACIAL PARALYSIS AND GAZE DEVIATION", which is incorporated by reference herein in its entirety

BACKGROUND

Various biological conditions can result in facial paralysis and/or gaze deviation. For example, cerebrovascular accidents, lesions of the brain, and nerve paralysis can result in gaze deviation. Additionally, Bell's palsy, a brain tumor, tick bites, or stroke can cause facial paralysis. With respect to stroke, intracranial blood vessels supply nutrients and oxygen to the brain comprising the cerebrum, cerebellum and brainstem. Some arteries supply blood to anterior portions of the brain, while other arteries supply blood to posterior portions of the brain. Disruption of the flow of blood to any part of the brain can have serious effects. The flow of blood to the brain can be interrupted by the narrowing and/or blockage of blood vessels supplying blood to the brain. The disruption of the flow of blood to parts of the brain can impair the function of the brain and result in numbness, weakness, or paralysis to parts of the body. Strokes can occur when blood supply to a portion of the brain is interrupted. Early detection and treatment of a stroke can minimize the damage to the portion(s) of the brain where blood supply was disrupted and minimize the aftereffects of the stroke.

BRIEF DESCRIPTION OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some implementations are illustrated by way of example, and not limitation.

DETAILED DESCRIPTION

Figure 1:
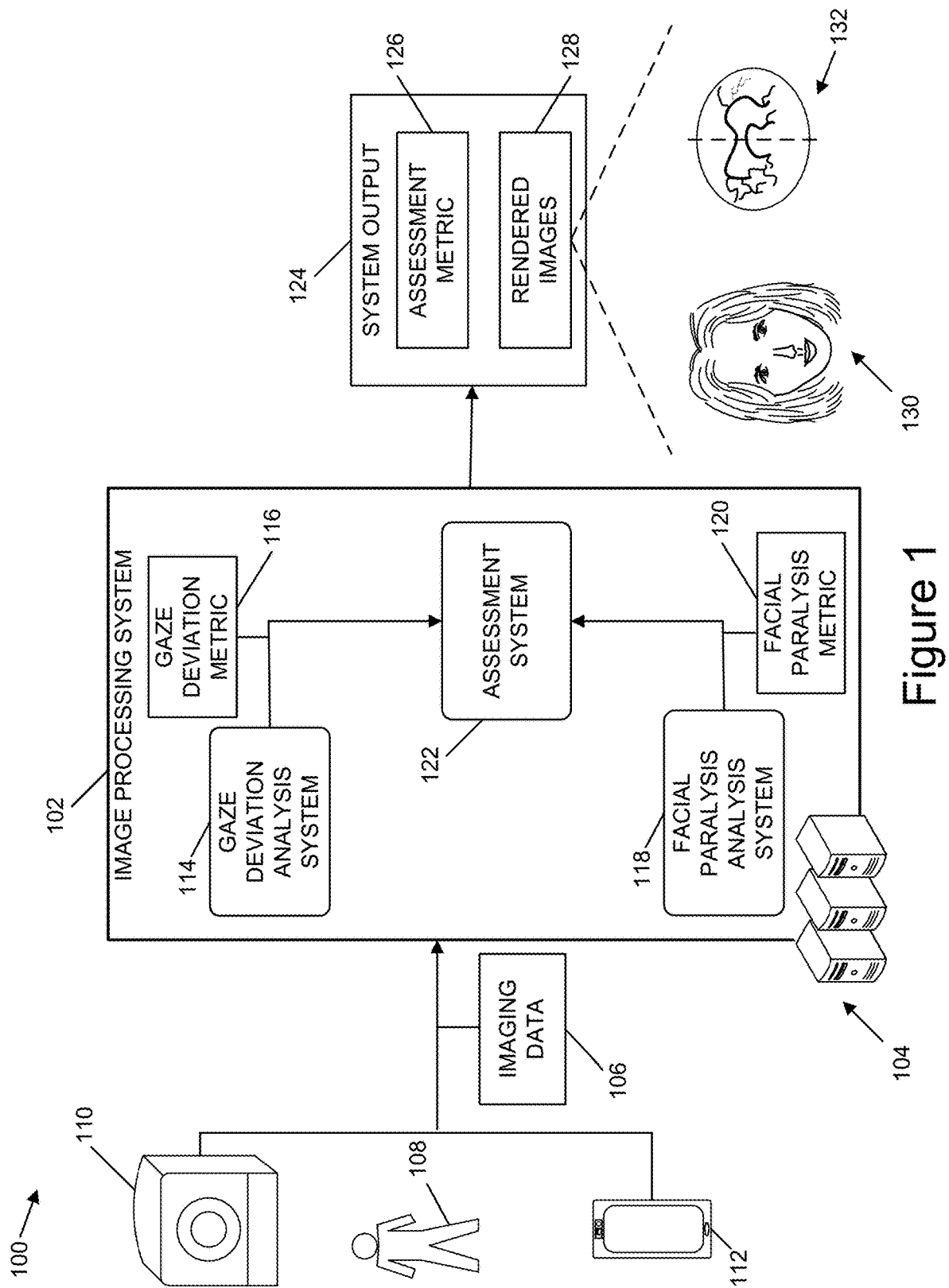
FIG. 1 is a diagrammatic representation of an architecture to determine measures of gaze deviation and facial paralysis based on imaging data, according to one or more example implementations.

Various imaging techniques can be performed to detect the presence (currently or in the past) of a biological condition that results in at least one of facial paralysis or stroke. In one or more examples, the biological condition can include a neurological condition. In one or more illustrative examples, the neurological condition can include a stroke in the brain of an individual.

In one or more implementations, computed tomography (CT) imaging techniques can be used to capture images of vessels that supply blood to the brain of an individual. Additionally, magnetic resonance (MR) imaging techniques can be used to capture images of blood vessels of the brain of an individual. Imaging techniques used to generate images of vessels that supply blood to the brain of an individual can include perfusion-based techniques and diffusion-based techniques. The images of blood vessels of the brain of an individual generated by one or more imaging techniques can be analyzed to determine regions of the brain of the individual in which an occluded vessel is present. Images of the brain of an individual generated by one or more imaging techniques can also be analyzed to identify regions of the brain of the individual that have been damaged due to lack of blood supply due to a blood vessel occlusion.

In addition to imaging-based techniques, clinicians can provide a diagnosis of a stroke based on observations made during examinations of the individuals by the clinicians. In situations where an occluded blood vessel causes a stroke, in addition to tissue damage that may occur due to the lack of blood flow, the electrophysiology of an individual may not function properly. In various examples, gaze deviation can be an indicator of stroke. Gaze deviation can be detected when an iris of at least one eye of an individual is offset with respect to a reference location. The direction of the gaze deviation can indicate a location of a stroke in the brain of the individual. For example, the gaze of an individual can point in the same direction as the side of the brain in which an occluded vessel is located. To illustrate, gaze deviation toward the right side (from the vantage point of facing the individual) can indicate an occluded vessel on the right side of the brain of the individual and gaze deviation toward the left side (from the vantage point of facing the individual) can indicate an occluded vessel on the left side of the brain of the individual.

Further, clinicians can observe facial paralysis in individuals experiencing a stroke. In some situations, an occluded blood vessel in the brain can cause paralysis of muscles in the face of an individual causing the appearance of one or more regions of the face of the individual to be altered. The changes in the facial appearance of individuals experiencing a stroke can result in facial droop. In various examples, muscles on the opposite side of the face can compensate for the facial droop causing the appearance on the opposite side of the face to also be altered. The side of the face in which the facial droop is occurring can indicate that the location of the stroke caused by a large vessel occlusion is in the opposite hemisphere of the brain of the individual. To illustrate, facial droop present on the right side of the face of an individual (from the vantage point of facing the individual) can indicate the presence of an occluded vessel in the left side of the brain of the individual and facial droop present on the left side of the face of the individual (from the vantage point of facing the individual) can indicate the presence of an occluded vessel in the right side of the brain of the individual.

Typically, images of a brain of an individual are analyzed by a trained specialist, such as a radiologist, to identify an occluded vessel and/or to determine damage to brain tissue. In some instances, radiologists receive medical records from clinicians that have examined the individual, but these medical records often do not indicate physical symptoms of the individual. Additionally, radiologists typically are unable to physically examine the individuals whose images the radiologists are examining. The accuracy and expediency in which a stroke is detected can impact the treatment administered to an individual and, also, the prognosis of the recovery of the individual. Thus, tools, techniques, systems, and methods that can provide additional information that can improve the accuracy of stroke detection can improve the treatment of the individuals and aid the recovery of the individuals that have suffered or are suffering a stroke.

The techniques, systems, processes, and methods described herein are directed to determining gaze deviation of individuals and facial paralysis of individuals based on imaging data. In various examples, the imaging data captured with respect to an individual can be analyzed with respect to reference imaging data or training imaging data. A gaze deviation metric can be determined based on the imaging data that indicates a measure of gaze deviation for the individual. Additionally, a facial paralysis metric can be determined based on the imaging data that indicates a measure of facial paralysis of the individual. In various examples, the gaze deviation metric and/or the facial paralysis metric can be used to determine a probability of an individual experiencing a stroke. The determination of metrics that indicate measures of gaze deviation and facial paralysis can help improve the accuracy of an assessment performed by a radiologist with respect to the presence or absence of an occluded vessel within a brain of an individual. In one or more examples, the metrics indicating measures of gaze deviation and facial paralysis can be used to augment imaging information that can indicate occlusions of blood vessels of individuals, such as images of blood vessels of the brains of individuals.

The imaging data used to determine the gaze deviation metrics and facial paralysis metrics can be captured by one or more imaging data sources. For example, the imaging data can be captured by one or more cameras of a computing device, such as a mobile phone, smart phone, tablet computing device, wearable device, or a laptop computing device. Additionally, the imaging data can be captured by a CT imaging device or an MR imaging device. In scenarios where the imaging data is captured by a CT imaging device or an MR imaging device, the techniques, systems, processes, and methods described herein perform a 3D rendering that corresponds to the outer features of the head of the individual, such as facial features of the individual. Thus, in contrast to the techniques implemented by existing systems that render the portions of the CT or MR imaging data that correspond to the inner portions of the brain of an individual, such as the blood vessels and other tissue, the techniques, systems, methods, and processes described herein are directed to rendering external features of the individual. In this way, a radiologist can have access to visual information with respect to an individual, almost as if the patient is in front of them, that is not present in existing systems that simply provide internal images of the brain of an individual. In various examples, coupling the external images of a face of an individual and metrics derived from the external images of the face of the individual with internal images of the brain of the individual can also increase the accuracy of diagnosis of the individual with respect to the presence or absence of a stroke. Further, since the techniques, systems, methods, and processes described herein can be implemented using a mobile computing device, an initial assessment with regard to facial paralysis and/or gaze deviation of a patient can be made by an emergency medical technician that is treating the patient. In this way, an initial assessment of the condition of the patient can be made prior to the patient seeing a trained specialist, such as a neurologist or emergency room physician.

FIG. 1 is a diagrammatic representation of an architecture 100 to determine measures of gaze deviation and facial paralysis based on imaging data, according to one or more example implementations. The architecture 100 can include an image processing system 102. The image processing system 102 can be implemented by one or more computing devices 104. The one or more computing devices 104 can include one or more server computing devices, one or more desktop computing devices, one or more laptop computing devices, one or more tablet computing devices, one or more mobile computing devices, or combinations thereof. In certain implementations, at least a portion of the one or more computing devices 104 can be implemented in a distributed computing environment. For example, at least a portion of the one or more computing devices 104 can be implemented in a cloud computing architecture.

The image processing system 102 can obtain imaging data 106 that is captured with respect to an individual 108. The imaging data 106 can include one or more data files that include data related to images captured by one or more imaging data sources. In one or more examples, the imaging data 106 can be formatted according to one or more imaging data formats, such as a Digital Imaging and Communication in Medicine (DICOM) format. In one or more additional examples, the imaging data 106 can be formatted according to at least one of a portable network graphics (PNG) format, a joint photographic experts group (JPEG) format, or a high efficient image format (HEIF). The imaging data 106 can be rendered by the image processing system 102 to generate one or more images that can be displayed on a display device. In various examples, the imaging data 106 can include a series of images of the individual 108 captured by one or more imaging data sources. In one or more illustrative examples, the imaging data 106 can correspond to one or more features of a head of the individual 108. In one or more scenarios, the imaging data 106 can be rendered to show external features of a head of the individual 108, such as at least a portion of a face of the individual 108. In one or more further instances, the imaging data 106 can be rendered to show internal features of the head of the individual 108, such as blood vessels or brain tissue located within the head of the individual 108.

The imaging data 106 can be captured by an imaging apparatus 110. The imaging device 106 can utilize one or more imaging technologies to capture the images 104. In one or more examples, the imaging apparatus 110 can implement computed tomography (CT) imaging techniques. In one or more further examples, the imaging apparatus 110 can implement magnetic resonance (MR) imaging techniques. MR imaging techniques implemented by the imaging apparatus 110 can include perfusion-based MR imaging techniques or diffusion-based MR imaging techniques. In situations where the imaging apparatus 110 implements CT-based imaging techniques or MR-based imaging techniques, the imaging data 106 can include thin-slice volumetric data.

The one or more imaging data sources can also include one or more computing devices 112. The one or more computing devices 112 can include at least one of a mobile computing device, a smart phone, a wearable device, a tablet computing device, or a laptop computing device. In one or more examples, the one or more computing devices 112 can generate a structured light pattern on at least a portion of the face of the individual 108 and capture one or more images of the individual 108 in relation to the structured light pattern. In these instances, the imaging data 106 can include a point cloud. In one or more additional examples, the one or more computing devices 112 can include one or more laser-based time-of-flight cameras. In these scenarios, the one or more computing devices 112 can include a light detecting and ranging (LiDAR) system. In one or more further examples, the one or more computing devices 112 can include multiple cameras and the imaging data 106 can correspond to stereo vision images. In one or more examples, the imaging data can also include random point clouds or sinusoidal patterns.

The image processing system 102 can include a gaze deviation analysis system 114. The gaze deviation analysis system 114 can analyze the imaging data 106 to determine whether a gaze of the individual 108 is different from the gaze of individuals that are not experiencing a stroke. For example, the gaze deviation analysis system 114 can determine a gaze deviation metric 116 for the individual 108. The gaze deviation metric 116 can indicate an offset of a gaze of at least one eye of the individual 108. The offset of the gaze of an eye of the individual 108 can be determined by analyzing a position of an iris of the eye of the individual 108 with respect to an expected position of the iris. The gaze deviation metric 116 can indicate an amount that the position of the iris of the eye of the individual 108 is different from the expected position of the iris. In various examples, the gaze deviation analysis system 114 can determine an angular offset of an iris of the individual 108 in degrees, such as 0.5 degrees, 1 degree, 2 degrees, 5 degrees, 10 degrees, 15 degrees, and so forth. The gaze deviation analysis system 114 can also determine a category indicating an amount of gaze deviation for the individual 108. In one or more illustrative examples, the gaze deviation metric 116 can indicate categories, such as "No Deviation", "Minor Deviation", and "Significant Deviation." The gaze deviation metric 116 can also include a directionality component, such as "Left" and "Right" indicating a direction that the iris of the individual 108 is pointing with respect to an expected direction. In these situations, the gaze deviation metric 116 can indicate "Minor Deviation, Left", "Minor Deviation, Right," and the like. In addition to the gaze deviation metric 116 being classified as categorical data, the gaze deviation metric can also be characterized as continuous or ordinal data.

The image processing system 102 can also include a facial paralysis analysis system 118. The facial paralysis analysis system 118 can analyze the imaging data 106 to determine whether the individual 108 is experiencing facial paralysis. In various examples, the facial paralysis analysis system 118 can analyze an appearance of the face of the individual 108 with respect to an expected appearance of faces of individuals that are not experiencing a stroke and an expected appearance of faces of individuals that are experiencing a stroke. In various examples, the facial paralysis analysis system 118 can determine a measure of similarity between an appearance of the face of the individual 108 with respect to the expected appearance of faces of individuals experiencing strokes and the expected appearance of faces of individuals that are not experiencing a stroke. In one or more illustrative examples, the facial paralysis analysis system 118 can analyze target regions of the face of the individual 108 to generate a facial paralysis metric 120. The facial paralysis metric 120 can indicate whether the characteristics of target regions of the face of the individual 108 are more like the characteristics of target regions of faces of individuals that are not experiencing a stroke or more like the characteristics of target regions of faces of individuals that are experiencing a stroke. The facial paralysis metric 120 can include a numerical metric indicating an amount of difference between characteristics of target regions of the face of the individual 108 and characteristics of target regions of faces of individuals experiencing a stroke. In various examples, the facial paralysis metric 120 can include categorical values indicating an amount of difference between characteristics of target regions of the face of the individual 108 and characteristics of target regions of faces of individuals experiencing a stroke. To illustrate, the facial paralysis metric 120 can include "No Paralysis", "Minor Paralysis", or "Significant Paralysis." The facial paralysis metric 120 can also include a directionality component, such as "Left" and "Right" indicating a side of the face of the individual 108 in which facial paralysis may be present. In these situations, the facial paralysis metric can indicate "Minor Paralysis, Left", "Minor Paralysis, Right," and the like.

The gaze deviation metric 116 and the facial paralysis metric 120 can be provided to an assessment system 122 of the image processing system 102. The assessment system 122 can analyze the gaze deviation metric 116 and the facial analysis metric 120 to determine a probability of the individual 108 experiencing a biological condition, such as a stroke or Bell's palsy. A probability of the individual 108 experiencing a biological condition can have a higher value based on a relatively higher value for at least one of the gaze deviation metric 116 or the facial paralysis metric 120. Additionally, a probability of the individual 108 experiencing a biological condition can have a lower value based on a relatively lower value for at least one of the gaze deviation metric 116 or the facial paralysis metric 120.

In one or more examples, the image processing system 102 can generate system output 124. The system output 124 can include an assessment metric 126 that corresponds to a probability that the individual 108 is experiencing a biological condition. As used herein, a biological condition can refer to an abnormality of function and/or structure in an individual to such a degree as to produce or threaten to produce a detectable feature of the abnormality. A biological condition can be characterized by external and/or internal characteristics, signs, and/or symptoms that indicate a deviation from a biological norm in one or more populations. A biological condition can include at least one of one or more diseases, one or more disorders, one or more injuries, one or more syndromes, one or more disabilities, one or more infections, one or more isolated symptoms, or other atypical variations of biological structure and/or function of individuals. In one or more illustrative examples, the one or more biological conditions can include one or more neurological conditions. In various examples, the system output 124 generated by the image processing system 102 can include user interface data that corresponds to a user interface that includes the assessment metric 126. The assessment metric 126 can indicate a numerical value of the probability of a biological condition being present in the individual 108. In one or more additional examples, the assessment metric 126 can indicate a categorical value of the probability of a biological condition being present in the individual 108. For example, the assessment metric 126 can include "No Biological Condition", "Minor Biological Condition Probability", "Significant Biological Condition Probability." In one or more illustrative examples, the assessment metric 126 can include "No Stroke", "Minor Stroke Probability", "Significant Stroke Probability."

The system output 124 can also include one or more rendered images 128. The one or more rendered images 128 can include one or more images of external features of the individual 108. For example, the one or more rendered images 128 can include a first image 130 of a face of the individual 108. Additionally, the one or more rendered images 128 can include one or more images of internal features of the individual 108. To illustrate, the one or more rendered images 128 can include a second image 132 of blood vessels of the brain of the individual 108. In one or more illustrative examples, the system output 124 can include a user interface that includes the first image 130 or the second image 132. In one or more additional examples, the system output 124 can include a user interface that includes both the first image 130 and the second image 132.

Additionally, in one or more further scenarios, the image processing system 102 can determine the assessment metric 126 based on an analysis of external features of the head of the individual 108 and internal features of the head of the individual 108. For example, the image processing system 102 can analyze characteristics of blood vessels of the brain of the individual 108 to determine a probability of the individual 108 experiencing a stroke. The image processing system 102 can combine the probability of a stroke being present in the individual 108 based on an analysis of blood vessels of the brain of the individual with a probability of a stroke being present in the individual 108 determined by the assessment system 122. In these instances, the output generated by the assessment system 122 can be complementary to an analysis by the image processing system of blood vessels of the brain of the individual 108. In various examples, combining the probability of a stroke being present in the individual 108 determined by the assessment system 122 with a probability of a stroke being present in the individual 108 determined based on an analysis of blood vessels of the brain of the individual 108 can increase an accuracy of the image processing system 102 in determining a probability of a stroke being present in the individual 108.

Although the illustrative example of FIG. 1 shows that the image processing system 102 includes both the gaze deviation analysis system 114 and the facial paralysis analysis system 118, in one or more additional implementations, the image processing system 102 can include the gaze deviation analysis system 114 or the facial paralysis system 118. In scenarios where the image processing system 102 includes the gaze deviation analysis system 114 and not the facial paralysis analysis system 118, the assessment system 122 can determine the assessment metric 126 using the gaze deviation metric 116 and not the facial paralysis metric 120. In additional instances where the image processing system 102 includes the facial paralysis analysis system 118 and not the gaze deviation analysis system 114, the assessment system 122 can determine the assessment metric 126 using the facial paralysis metric 120 and not the gaze deviation metric 116.

Figure 2:
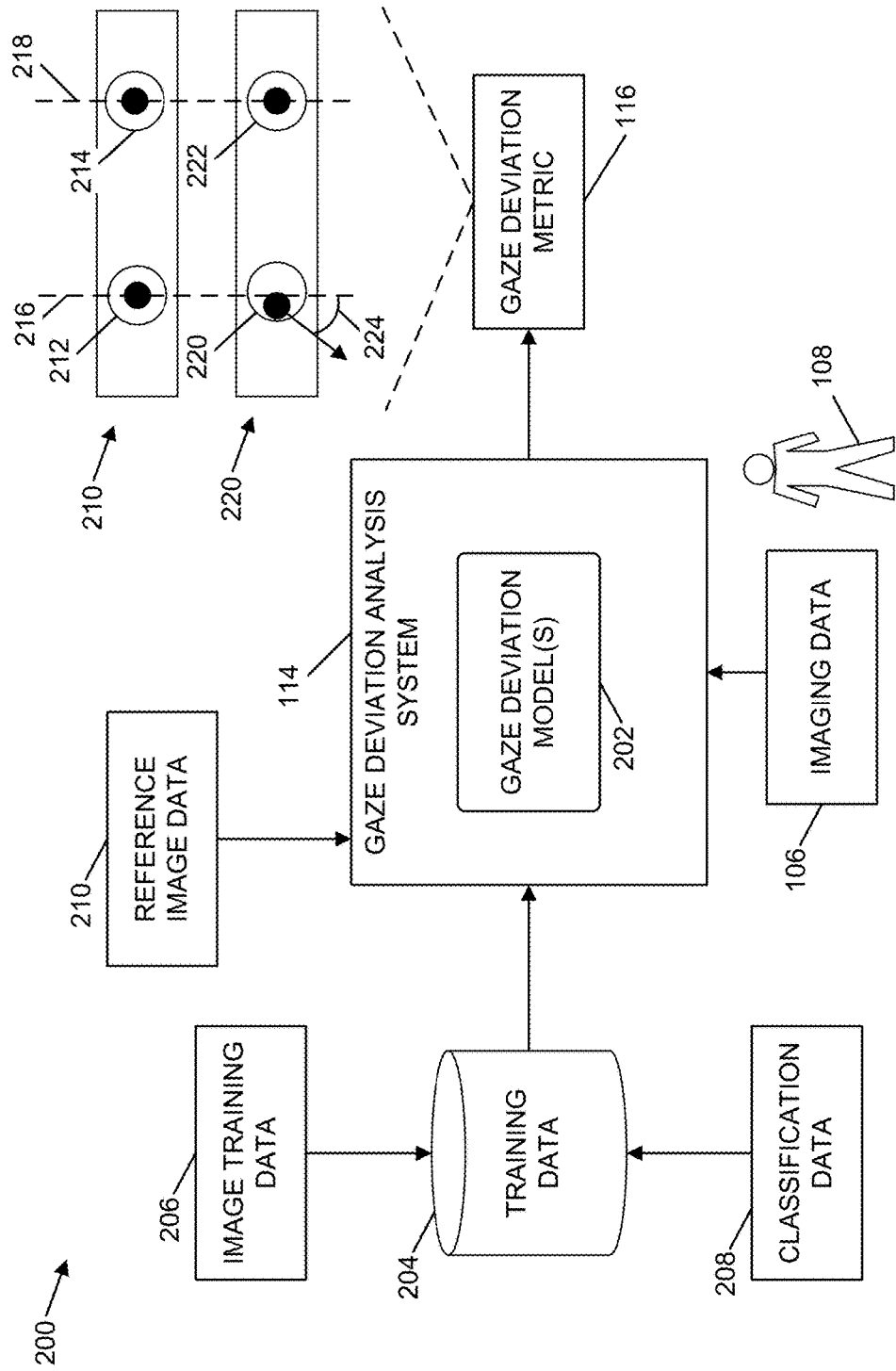
FIG. 2 is a diagrammatic representation of an architecture to determine an amount of gaze deviation of an individual based on imaging data, according to one or more example implementations.

FIG. 2 is a diagrammatic representation of an architecture 200 to determine an amount of gaze deviation of an individual based on imaging data, according to one or more example implementations. The architecture 200 can include the gaze deviation analysis system 114. The gaze deviation analysis system 114 can include one or more gaze deviation models 202. The one or more gaze deviation models 202 can be implemented to generate the gaze deviation metric 116. The one or more gaze deviation models 202 can be generated using one or more machine learning techniques. The one or more machine-learning techniques can include one or more classification-based machine learning techniques. In various examples, the one or more machine learning techniques can include supervised classification-based machine learning techniques. The one or more supervised classification-based machine learning techniques can include at least one of one or more logistic regression algorithms, one or more Naïve Bayes algorithms, one or more K-nearest neighbor algorithms, or one or more support vector machine algorithms. In one or more additional examples, the one or more machine learning techniques used to generate the one or more gaze deviation models 202 can include one or more residual neural networks. In one or more further examples, the one or more machine learning techniques used to generate the one or more gaze deviation models 202 can include at least one of one or more u-net convolutional networks, one or more v-net convolutional neural networks, or one or more residual neural networks (ResNet). In one or more illustrative example, a combination of machine learning techniques can be used to generate the one or more gaze deviation models 202. To illustrate, one or more residual neural networks and one or more u-net convolutional networks can be used to generate the one or more gaze deviation models 202.

In one or more implementations, the one or more gaze detection models 202 can be training using training data 204. The training data 204 can include image training data 206. In various examples, the image training data 206 can include images of faces of a number of different individuals. At least a portion of the image training data 206 can include images captured of individuals that experienced a biological condition. Additionally, at least a portion of the image training data 206 can include images captured of individuals that did not experience a biological condition. In one or more illustrative examples, the training date 206 can include a series of images of a number of individuals that move their eyes is various directions and to varying degrees. The training data 204 can also include classification data 208 indicating respective images included in the image training data 206 that correspond to individuals that experienced a biological condition and additional images included in the image training data 206 that correspond to individuals that did not experience a biological condition. Further, the training data 204 can include a number of images that can be used to validate the one or more gaze deviation models 202. In one or more illustrative examples, a convolutional neural network having an 80/20 split using 5-fold validation can be trained using the training data 206 to generate the one or more gaze deviation models 202.

In various examples, the one or more gaze deviation models 202 can be trained to identify images in which a gaze of an individual is offset with respect to an expected gaze. In one or more examples, the expected gaze can correspond to the gaze of individuals in which a stroke is not present when the individuals are looking straight forward at an object. The one or more gaze deviation models 202 can determine an expected gaze of an individual by analyzing images included in the image training data 206 of individuals in which a biological condition is not present who are looking straight forward at an object to determine features of the eyes of the individuals. In one or more illustrative examples, the one or more gaze deviation models 202 can determine that an expected gaze of an individual in which a biological is not present is a gaze in which the irises of the individual are aligned with respective vertical axes. FIG. 2 includes an example expected gaze 210 with a first iris 212 and a second iris 214 being aligned along a first vertical axis 216 and a second vertical axis 218, respectively.

The one or more gaze deviation models 202 can also be trained to determine features of eyes of individuals in which gaze deviation is present. Gaze deviation can be determined as a gaze of an individual that has at least a threshold amount of difference from the expected gaze. The threshold amount of difference can include at least a minimum angular offset in relation to a respective vertical axis. The minimum angular offset can be at least about 0.5 degrees, at least about 1 degree, at least about 2 degrees, at least about 3 degrees, at least about 4 degrees, or at least about 5 degrees. In one or more illustrative examples, the minimum angular offset can be from about 0.5 degrees to about 5 degrees, from about 1 degree to about 3 degrees, or from about 0.5 degrees to about 2 degrees. After training and validation of the one or more gaze deviation models 202, the one or more gaze deviation models 202 can be implemented to classify the imaging data 106 of the individual 108.

The one or more gaze deviation models 202 can generate the gaze deviation metric 116 based on the imaging data 106. The illustrative example of FIG. 2 includes an example gaze 220 derived from the imaging data 106. The example gaze 220 includes a third iris 220 and a fourth iris 222. The example gaze 220 indicates that the third iris 220 is offset with respect to the first vertical axis 216 by an angular offset 224. The example gaze 220 also indicates that the fourth iris 222 is aligned with the second vertical axis 222 with no angular offset. The one or more gaze deviation models 202 can determine whether the angular offset 224 is greater than a minimum angular offset. In situations where the angular offset 224 is greater than the minimum angular offset, the one or more gaze deviation models 202 can classify the individual 108 as having a gaze deviation that corresponds to at least a minimum probability of the individual 108 experiencing a stroke. In various examples, the extent of the angular offset 224 beyond the minimum angular offset can indicate the magnitude of the probability of a stroke being present in the individual 108. For example, as the angular offset 224 increases, a probability of the individual 108 experiencing a stroke can also increase. Additionally, as the angular offset 224 increases, a severity of a stroke can also increase. Although the illustrative example of FIG. 2 indicates the angular offset 224 with respect to the third iris 220, in other examples, an additional angular offset can be present with respect to the fourth iris 222. Additionally, both the third iris 220 and the fourth iris 222 can be offset. In one or more examples, the additional angular offset of the fourth iris 222 can be the same as the angular offset 224. In one or more further examples, the angular offset of the fourth iris 222 can be different from the angular offset 224.

In one or more additional examples, the one or more gaze deviation models 202 can determine an amount of gaze deviation of the individual 108 based on reference image data 210. In one or more examples, the reference image data 210 can include one or more images of the individual 108 captured during a period of time in which the individual 108 was not experiencing a biological condition. In these scenarios, the one or more gaze deviation models 202 can analyze the imaging data 106 with respect to the reference image data 210 to determine an amount of difference between the gaze of the individual 108 included in the reference image data 210 and the gaze of the individual 108 included in the imaging data 106. In various examples, the expected gaze 210 can correspond to the gaze of the individual 108 determined based on the reference image data 210.

In one or more examples, before being processed by the one or more gaze deviation models 202, the training data 204 and the imaging data 106 can be preprocessed by the gaze deviation analysis system 114 or the image processing system 102 of FIG. 1. For example, one or more computational techniques can be applied to the training data 204 and the imaging data 106 to generate a modified dataset that is processed according to the one or more machine learning techniques implemented by the one or more gaze deviation models 202. In scenarios where at least one of the training data 204 or the imaging data 106 includes three-dimensional volumetric data from CT-based imaging devices or MR-based imaging devices, a 3-dimensional (3D) rendering can be performed. A 3D rendering can also be performed with in respect to data captured via a LiDAR system, a time of flight system, and/or a point cloud/structured light system. The 3D rendering can include a volume rendering or a surface rendering. In one or more illustrative examples, a binary mask can be generated from images included in at least one of the training data 204 or the imaging data 106. The binary mask can indicate voxels of the images that are foreground voxels and background voxels. Additionally, a mesh of polygons can be generated using the binary mask that corresponds to a surface of an object included in the images, such as the face of individuals that correspond to the images. The mesh of polygons can be rendered to produce images of the faces of individuals that can be analyzed by the one or more gaze deviation models 202.

Images derived from the training data 204 and the imaging data 106 can also be processed to identify the eyes of individuals. In one or more examples, the classification data 208 can identify the eyes of individuals included in images of the image training data 206. In this way, the one or more gaze deviation models 202 can be trained to identify the eyes of individuals. In one or more additional examples, a filter can be generated that can be used to identify the eyes of individuals. The filter to identify the eyes of individuals can be generated based on the training data 204. In various examples, the gaze deviation analysis system 114 can determine that at least one eye of the individual 108 is not able to be identified. In these situations, the gaze deviation analysis system 114 can provide an indication that the gaze deviation analysis system 112 is unable to analyze the imaging data 106. In one or more examples, at least one eye of the individual 108 can be blocked by an object, such as sunglasses, hair, and the like.

Additionally, at least one of the training data 204 or the imaging data 106 can be augmented before being processed by the one or more gaze deviation models 202. In one or more examples, volumetric data obtained from MR-based imaging devices, CT-based imaging devices, LiDAR systems, time of flight systems, structured light systems, or images captured by a mobile device camera from a number of different vantage points can be used to generate a number of images that correspond to multiple vantage points. In this way, the gaze of individuals and facial paralysis can be analyzed from a number of vantage points. In one or more additional examples, one or more vantage points can be identified that provide an image of the gaze of the individuals that can be processed by the one or more gaze deviation models 202 to increase the accuracy of the gaze deviation metric 116. For example, one or more images related to a vantage point showing the individual facing forward and looking forward can be selected for processing by the one or more gaze deviation models rather than images with vantage points where individuals are looking to one side or are not facing forward. In one or more further examples, at least one of the training data 204 or the imaging data 106 can include multiple images of individuals corresponding to different vantage points. To illustrate, one or more cameras of a computing device can be used to obtain images of individuals from different vantage points (in relation to the orientation of the computing device), such as one or more right side vantage points, one or more left side vantage points, or a front facing vantage point. In these instances, images corresponding to forward facing vantage points can be selected for analysis by the one or more gaze deviation models 202.

Although the gaze deviation of an individual is discussed with respect to FIG. 2 in relation to an iris of an individual, gaze deviation can also be determined based on a location of a pupil of an individual.

Figure 3:
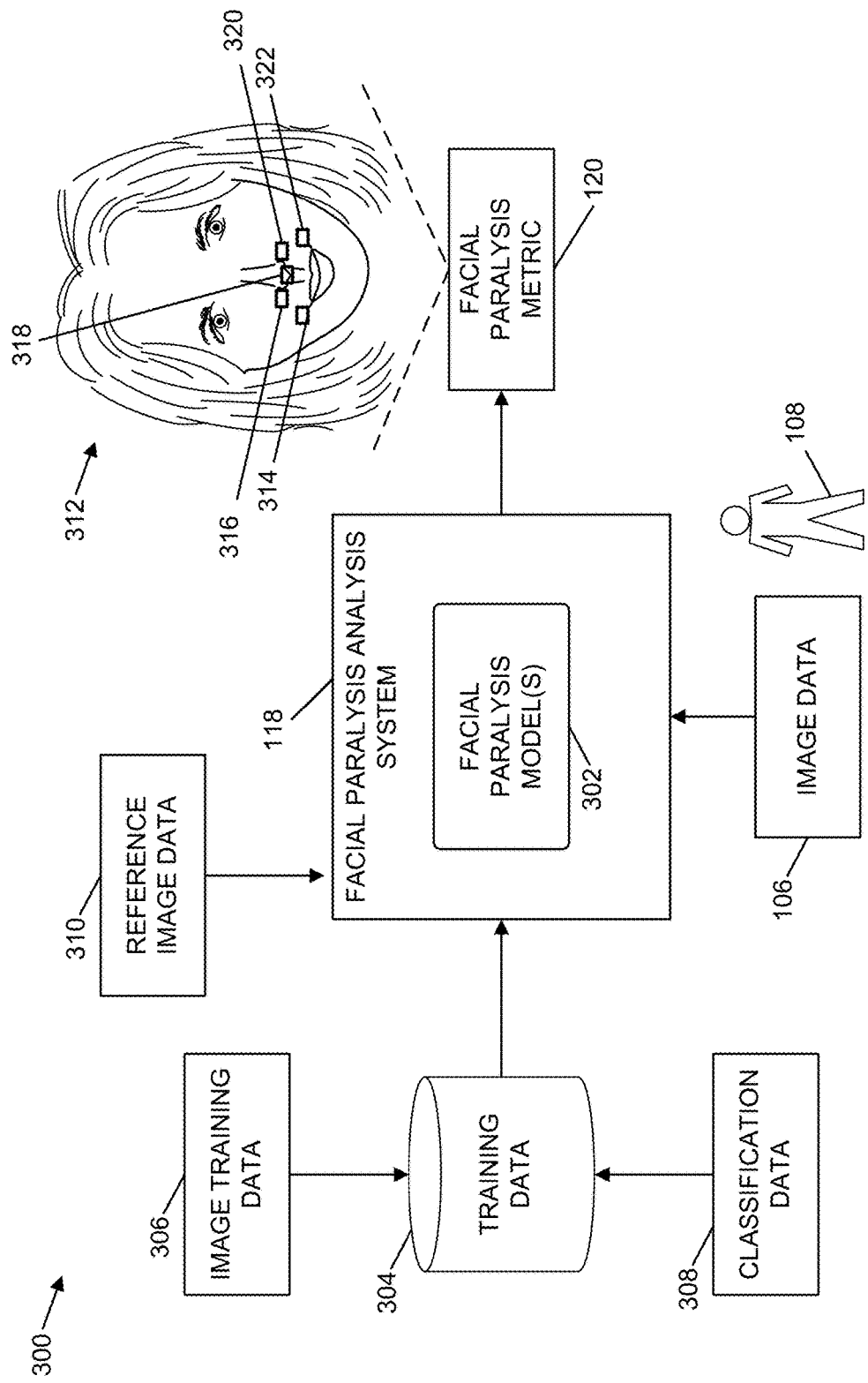
FIG. 3 is a diagrammatic representation of an architecture to determine an amount of facial paralysis of an individual based on imaging data, according to one or more example implementations.

FIG. 3 is a diagrammatic representation of an architecture 300 to determine an amount of facial paralysis of an individual, according to one or more example implementations. The architecture 300 can include the facial paralysis analysis system 118. The facial paralysis analysis system 118 can include one or more facial paralysis models 302. The one or more facial paralysis models 302 can be implemented to generate the facial paralysis metric 120. The one or more facial paralysis models 302 can be generated using one or more machine learning techniques. The one or more machine-learning techniques can include one or more classification-based machine learning techniques. In various examples, the one or more machine learning techniques can include supervised classification-based machine learning techniques. The one or more supervised classification-based machine learning techniques can include at least one of one or more logistic regression algorithms, one or more Naïve Bayes algorithms, one or more K-nearest neighbor algorithms, or one or more support vector machine algorithms. In one or more additional examples, the one or more machine learning techniques used to generate the one or more facial paralysis models 302 can include one or more residual neural networks. In one or more further examples, the one or more machine learning techniques used to generate the one or more facial paralysis models 302 can include one or more u-net convolutional networks, one or more v-net convolutional neural networks, or one or more residual neural networks (ResNet). In one or more illustrative example, a combination of machine learning techniques can be used to generate the one or more facial paralysis models 302. To illustrate, one or more residual neural networks and one or more u-net convolutional networks can be used to generate the one or more facial paralysis models 302.

In one or more implementations, the one or more facial paralysis models 302 can be trained using training data 304. The training data 304 can include image training data 306. In various examples, the image training data 306 can include images of faces of a number of different individuals. At least a portion of the image training data 306 can include images captured of individuals experiencing a biological condition. Additionally, at least a portion of the image training data 306 can include images captured of individuals that are not experiencing a biological condition. The training data 304 can also include classification data 308 indicating respective images included in the image training data 306 that correspond to individuals experiencing a biological condition and additional images included in the image training data 306 that correspond to individual that are not experiencing a biological condition. Further, the training data 304 can include a number of images that can be used to validate the one or more facial paralysis models 302. In one or more illustrative examples, a convolutional neural network having an 80/20 split using 5-fold validation can be trained using the training data 306 to generate the one or more facial paralysis models 302.

In various examples, the one or more facial paralysis models 302 can be trained to identify target regions of faces of individuals. The target regions can be regions of faces of individuals that can indicate facial paralysis. The one or more facial paralysis models 302 can be trained to determine characteristics of the target regions that indicate facial paralysis. In one or more examples, the one or more facial paralysis models can be trained to determine an amount of facial droop on one side of the faces of individuals. The one or more facial paralysis models 302 can analyze images of individuals that are not experiencing a stroke and images of individuals that are experiencing a stroke to determine differences in characteristics of the target regions in individuals experiencing a stroke and those that are not experiencing a stroke. In one or more scenarios, the characteristics of target regions of individuals that are experiencing a stroke can be shifted with respect to characteristics of target regions of individuals that are not experiencing a stroke. The facial paralysis metric 120 can indicate an amount of similarity between characteristics of target regions of individuals included in images being analyzed by the facial paralysis analysis system 118 with respect to characteristics of target regions of individuals that are experiencing a stroke. In one or more illustrative examples, the facial paralysis metric 120 can indicate a measure of facial paralysis of individuals, such as at least one of a numerical value or a categorical value.

In this way, the one or more facial paralysis models 302 can analyze the image data 106 to determine whether the characteristics of the target regions of the face of the individual 108 correspond to characteristics of target regions of individuals experiencing a biological condition or correspond to characteristics of target regions of individuals that are not experiencing a biological condition. In the illustrative example of FIG. 3, an image 312 can be rendered based on the image data 106. The one or more facial paralysis models 302 can analyze characteristics of a number of target regions of the face of the individual 108 including a first target region 314, a second target region 316, a third target region 318, a fourth target region 320, and a fifth target region 322. The one or more facial paralysis models 302 can analyze the target regions 314, 316, 318, 320, 322 to determine one or more characteristics of the target regions 314, 316, 318, 320, 322 of the individual 108. In addition, the one or more facial paralysis models 302 can determine the facial paralysis metric 120 for the individual 108 based on the characteristics of the target regions 314, 316, 318, 320, 322 for the individual 108.

In one or more additional examples, the one or more facial paralysis models 302 can determine an amount of facial paralysis of the individual 108 based on reference image data 310. In one or more examples, the reference image data 310 can include one or more images of the individual 108 captured during a period of time in which the individual 108 was not experiencing a stroke. In these scenarios, the one or more facial paralysis models 302 can analyze the imaging data 106 with respect to the reference image data 310 to determine an amount of difference between the characteristics of the target regions 314, 316, 318, 320, 322 of the individual 108 included in the reference image data 310 and the characteristics of the target regions 314, 316, 318, 320, 322 of the individual 108 that are determined based on the imaging data 106.

Further, the one or more facial paralysis models 302 can determine an amount of facial paralysis of the individual 108 by analyzing characteristics of at least a portion of the target regions 314, 316, 318, 320, 322 on opposing sides of the face of the individual 108. For example, the one or more facial paralysis models 302 can analyze characteristics of the first target region 314 with respect to the characteristics of the fifth target region 322. Additionally, the one or more facial paralysis models 302 can analyze characteristics of the second target region 316 with respect to the characteristics of the fourth target region 320, the one or more facial paralysis models 302 can determine an amount of facial paralysis of the individual 308 based on an amount of differences between the characteristics of the first target region 314 and the fifth target region 322 and/or an amount of differences between the characteristics of the second target region 316 and the fourth target region 320.

In one or more examples, before being processed by the one or more facial paralysis models 302, the training data 304 and the imaging data 106 can be preprocessed by the facial paralysis analysis system 118 or the image processing system 102 of FIG. 1. For example, one or more computational techniques can be applied to the training data 304 and the imaging data 106 to generate a modified dataset that is processed according to the one or more machine learning techniques implemented by the one or more facial paralysis models 302. In scenarios where at least one of the training data 304 or the imaging data 106 includes three-dimensional volumetric data from CT-based imaging devices or MR-based imaging devices, a 3-dimensional rendering can be performed. In one or more illustrative examples, a binary mask can be generated from images included in at least one of the training data 304 or the imaging data 106. The binary mask can indicate voxels of the images that are foreground voxels and background voxels. Additionally, a mesh can be generated using the binary mask that corresponds to a surface of an object included in the images, such as the face of individuals that correspond to the images. The mesh can be rendered to produce images of the faces of individuals that can be analyzed by the one or more facial paralysis models 302. In various examples, the mesh can include a mesh of polygons. Additionally, the 3D rendering can include volume rendering techniques or surface rendering techniques. In one or more additional examples, the preprocessing can be performed without generating the binary mask.

Images derived from the training data 304 and the imaging data 106 can also be processed to identify the target regions, such as target regions 314, 316, 318, 320, 322, of individuals. In one or more examples, the classification data 308 can identify the target regions. In this way, the one or more facial paralysis models 302 can be trained to identify the target regions of individuals. In one or more additional examples, a filter can be generated that can be used to identify the target regions of individuals. The filter to identify the target regions of individuals can be generated based on the training data 304. In various examples, the facial paralysis analysis system 118 can determine that at least one of the target regions 314, 316, 318, 320, 322 of the individual 108 is not able to be identified or is distorted. In these situations, the facial paralysis analysis system 118 can provide an indication that the facial paralysis analysis system 118 is unable to analyze the imaging data 106. In one or more examples, at least one eye of the individual 108 can be blocked by an object, such as an oxygen mask, glasses, and the like.

Additionally, at least one of the training data 304 or the imaging data 106 can be augmented before being processed by the one or more facial paralysis models 302. In one or more examples, volumetric data obtained from MR-based imaging devices or CT-based imaging devices can be used to generate a number of images that correspond to multiple vantage points. In this way, the characteristics of target regions of individuals can be analyzed from a number of vantage points. In one or more additional examples, one or more vantage points can be identified that provide an image of at least a portion of the target regions of the individuals that can be processed by the one or more facial paralysis models 302 to increase the accuracy of the facial paralysis metric 120. For example, one or more images related to a vantage point showing the individual facing forward and looking forward can be selected for processing by the one or more facial paralysis models 302 rather than images with vantage points where individuals are looking to one side or are not facing forward. In one or more further examples, at least one of the training data 304 or the imaging data 106 can include multiple images of individuals corresponding to different vantage points. To illustrate, one or more cameras of a computing device can be used to obtain images of individuals from different vantage points (in relation to the orientation of the computing device), such as one or more right side vantage points, one or more left side vantage points, or a front facing vantage point. In these instances, images corresponding to forward facing vantage points can be selected for analysis by the one or more facial paralysis models 302. In various examples, a computing device being used to capture the image data 106 for the individual 108 and/or to capture the image training data 306 can include a user interface guide, such as an outline, that enables a user of the computing device to align the faces of individuals with the user interface guide. In this way, the image training data 306 and the image data 106 can be standardized resulting in the image data 106 being processed more accurately and efficiently by the facial paralysis analysis system 118.

Figure 4:
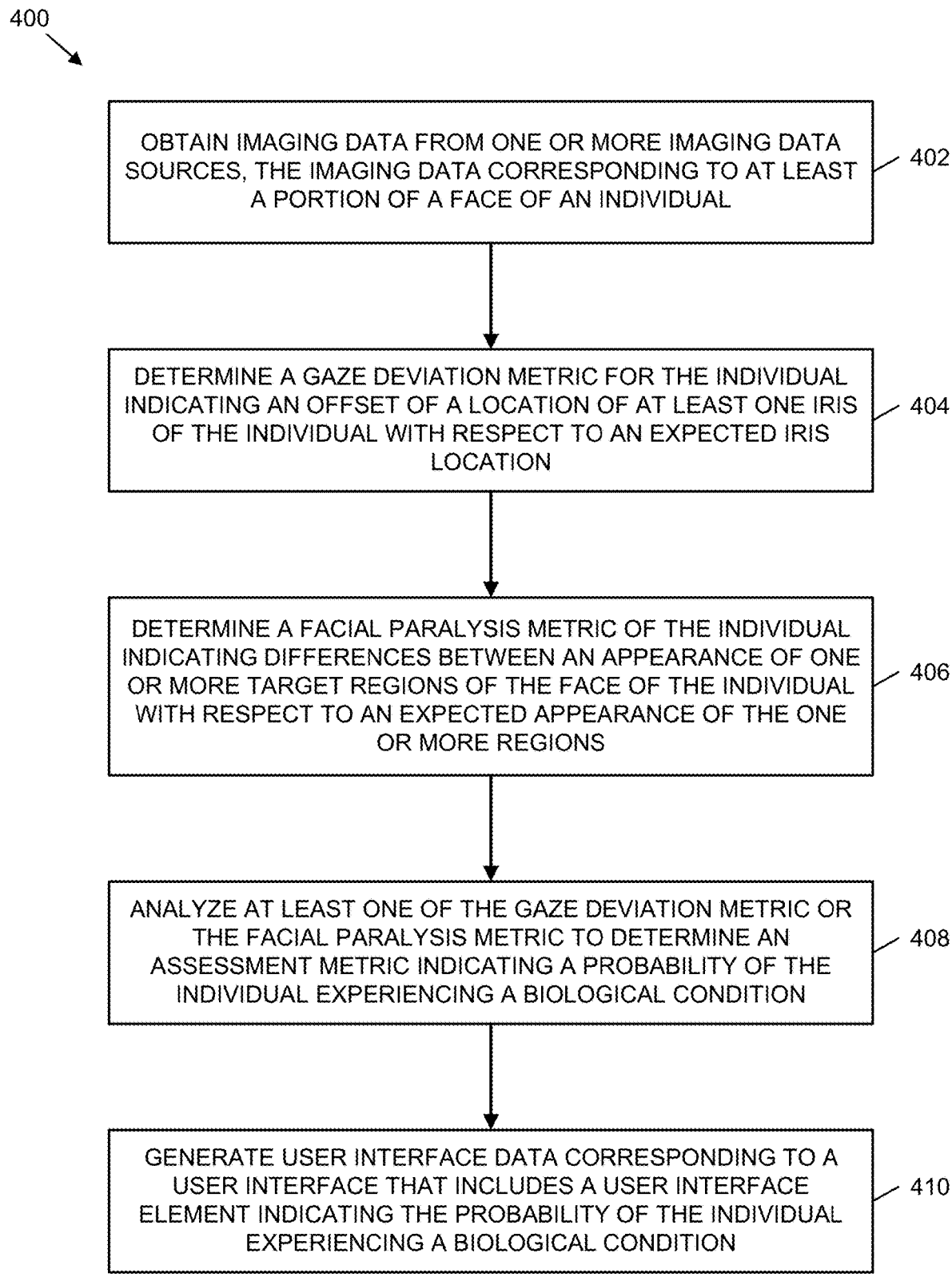
FIG. 4 is a flowchart illustrating example operations of a process to analyze an amount of gaze deviation and facial paralysis of an individual to determine a probability of the individual experiencing a biological condition, according to one or more example implementations.

FIG. 4 illustrate flowcharts of processes to analyze images of faces of individuals to generate an assessment of whether the individuals are experiencing a stroke. The processes may be embodied in computer-readable instructions for execution by one or more processors such that the operations of the processes may be performed in part or in whole by the functional components of the image processing system 102. Accordingly, the processes described below are by way of example with reference thereto, in some situations. However, in other implementations, at least some of the operations of the processes described with respect to FIG. 4 may be deployed on various other hardware configurations. The processes described with respect to FIG. 4 are therefore not intended to be limited to the image processing system 102 and can be implemented in whole, or in part, by one or more additional components. Although the described flowcharts can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems.

FIG. 4 is a flowchart illustrating example operations of a process 400 to analyze an amount of gaze deviation and facial paralysis of an individual to determine a probability of the individual experiencing a stroke, according to one or more example implementations. At operation 402, the process 400 can include obtaining imaging data from one or more imaging sources. The imaging data can correspond to at least a portion of a face of an individual. The one or more imaging sources can include a MR-based imaging apparatus or a CT-based imaging apparatus. The CT-based imaging apparatus can include, in one or more examples, a CT-angiogram imaging apparatus or a CT-perfusion imaging apparatus. Additionally, the one or more imaging sources can include one or more computing devices, such as a smart phone, a wearable device, a mobile computing device, a laptop computing device, or a tablet computing device. In these scenarios, the imaging data can be captured by one or more cameras of the one or more computing devices. In various examples, a stereoscopic camera system of the one or more computing devices can be used to capture the imaging data. In one or more additional examples, the one or more computing devices can generate a structured light pattern and capture one of more images of the individual with respect to the structured light pattern. The one or more imaging sources can also include time of flight cameras, LiDAR systems, and/or stereovision cameras.

At operation 404, the process 400 can include determining, based on the image data, a gaze deviation metric for the individual. The gaze deviation metric can indicate an offset of a location of at least one iris of the individual with respect to an expected iris location. In addition, the process 400 can include, at operation 406, determining, based on the imaging data, a facial paralysis metric of the individual. The facial paralysis metric can indicate differences between an appearance of one or more target regions of the face of the individual with respect to an expected appearance of the one or more target regions.

In various examples, one or more machine learning techniques can be implemented to determine the gaze deviation metric and the facial paralysis metric. In one or more examples, one or more convolutional neural networks can be trained to determine the gaze deviation metric and the facial paralysis metric. The training data for the one or more convolutional neural networks can include a first set of images of first individuals that experienced a biological condition that resulted in an amount of gaze deviation. The training data for the one or more convolutional neural networks can also include a second set of images of second individuals that experienced biological condition that resulted in an amount of facial paralysis. Further, the training data for the one or more convolutional neural networks can include a third set of images of third individuals that did not experience a biological condition, that did not have an amount of gaze deviation, and that did not have an amount of facial paralysis. The training data can also include an additional set of images of an additional group of individuals that experienced both gaze deviation and facial paralysis. The training data can also include characteristics of the individuals, such as ethnic background, age, gender, presence of glasses, presence of facial hair, and the like. In one or more further examples, the training data can be obtained from a same individual captured at a previous point in time before the individual was experiencing the biological condition. In one or more examples, the training data can include classification data indicating the images where gaze deviation is present, the images where facial paralysis is present, and the images where neither gaze deviation nor facial paralysis are present. In one or more illustrative examples, the output of the one or more convolutional networks can include a plurality of categories with respect to gaze deviation and a plurality of categories with respect to facial paralysis. In one or more further examples, one or more convolutional neural networks can be trained to determine a feature set that is indicative of gaze deviation and a feature set that is indicative of facial paralysis. The feature set may not include one or more target regions. In these scenarios, the one or more convolutional neural networks can analyze new images of patients with respect to the respective feature sets to determine amounts of similarity between the feature sets and the new images to determine a measure of gaze deviation and/or a measure of facial paralysis.

In one or more examples, training data can be determined from a number of vantage points. The vantage points can include images taken from a number of different positions with respect to an individual. The number of vantage points can also be determined in silico, such as extracted MR or CT data related to the different vantage points.

The process 400 can also include, at operation 408, analyzing at least one of the gaze deviation metric or the facial paralysis metric to determine an assessment metric indicating a probability of a presence of a biological condition with respect to the individual. In various examples, as the gaze deviation metric increases, the assessment metric can also increase because the more pronounced the gaze deviation for the individual, the higher the probability that the individual is experiencing the biological condition. Additionally, as the facial paralysis metric increases, the assessment metric can also increase because as the amount of facial paralysis increases, the probability that the individual is experiencing a biological condition also increases. The amount of gaze deviation and/or the amount of facial paralysis can also be indicators of severity of a biological condition experienced by the individual. In one or more examples, the biological condition can include a neurological condition, such as Bell's palsy or stroke.

Further, at operation 410, the process 400 can include generating user interface data corresponding to one or more user interfaces that include a user interface element indicating the probability of the presence of the biological condition with respect to the individual. In one or more examples, the assessment metric can be displayed in the user interface as a numerical probability. In one or more additional examples, the assessment metric can be displayed in the user interface as a categorical indicator. The one or more user interfaces can also include an image of the face of the individual that is rendered based on the imaging data and on which the gaze deviation metric and the facial paralysis metric are determined. In addition to the facial image of the individual an image of the brain of the individual can also be displayed. For example, an image showing blood vessels of the brain of the individual can also be displayed in the one or more user interfaces. In this way, images of external portions of individuals and images of internal portions of individuals can be rendered from the same imaging data and used to determine a probability of an individual experiencing a biological condition.

In one or more illustrative examples, the images can be captured of an individual using a mobile computing device, such an EMT or other medical personnel. The screen of the mobile computing device can include an outline and the image of the individual shown in the user interface can be aligned with the outline. In one or more examples, a number of images can be captured from different vantage points. In these scenarios, the image data captured by the mobile computing device can be analyzed to determine an amount of facial paralysis of the individual and/or an amount of gaze deviation of the individual. Additionally, an initial assessment of the individual can be determined with respect to a biological condition can be determined based on the amount of gaze deviation and/or the amount of facial paralysis.

Figure 5:
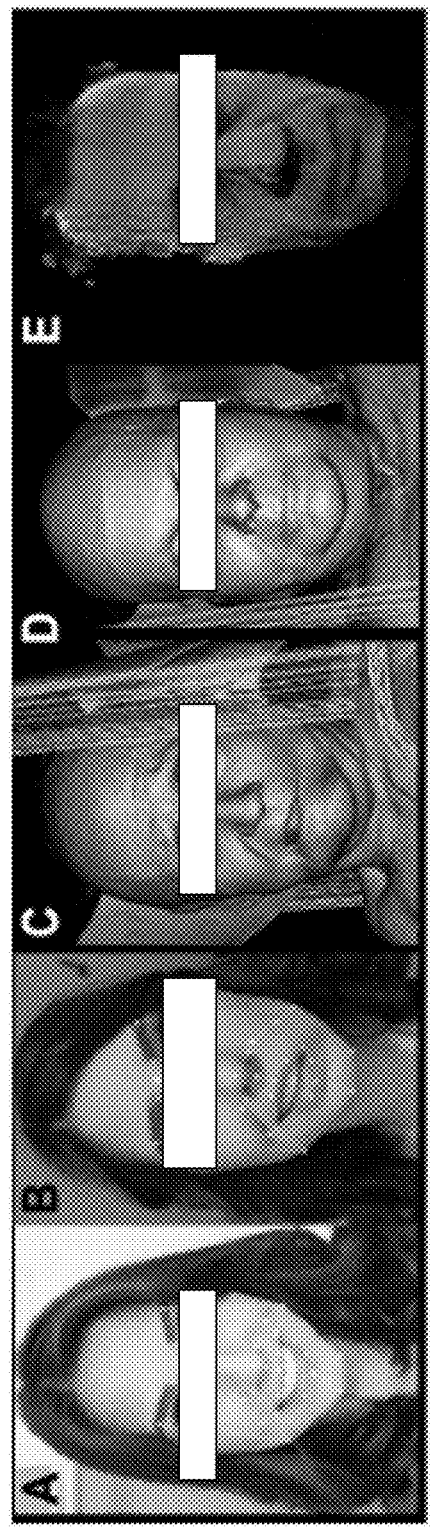
FIG. 5 includes a number of images that indicate individuals that are not experiencing facial paralysis and individuals experiencing facial paralysis.

FIG. 5 includes a number of images that indicate individuals that are not experiencing facial paralysis and individuals experiencing facial paralysis. Image A includes an image of an individual prior to experiencing a stroke and Image B includes an image of the same individual after experiencing a stroke with left side facial paralysis and gaze deviation in the left eye that is to the right. Image C includes a volume rendering of CT volume data of an 88-year old individual experiencing a right side proximal intracranial artery (ICA) occlusion with facial paralysis on the left side. Image D includes a volume rendering of CT volume data of an 82-year old patient with occlusion of the right superior M2 region of the middle cerebral artery (MCA) with left facial paralysis and mild conjugate gaze deviation to the right side. Image E includes a photographic overlay of the face of an individual on a surface rendering obtained with a three-dimensional structured light camera.

Figure 6:
FIG. 6 includes images rendered using computed tomography data of a face of an individual where the different images correspond to different vantage points of the face of the individual.

FIG. 6 includes images rendered using computer tomography data of a face of an individual where the different images correspond to different vantage points of the face of the individual. The images included in FIG. 6 are from 9 different vantage points rendered from CT volume data of an 80-year old patient with an occlusion in the right distal portion of the ICA.

Figure 7:
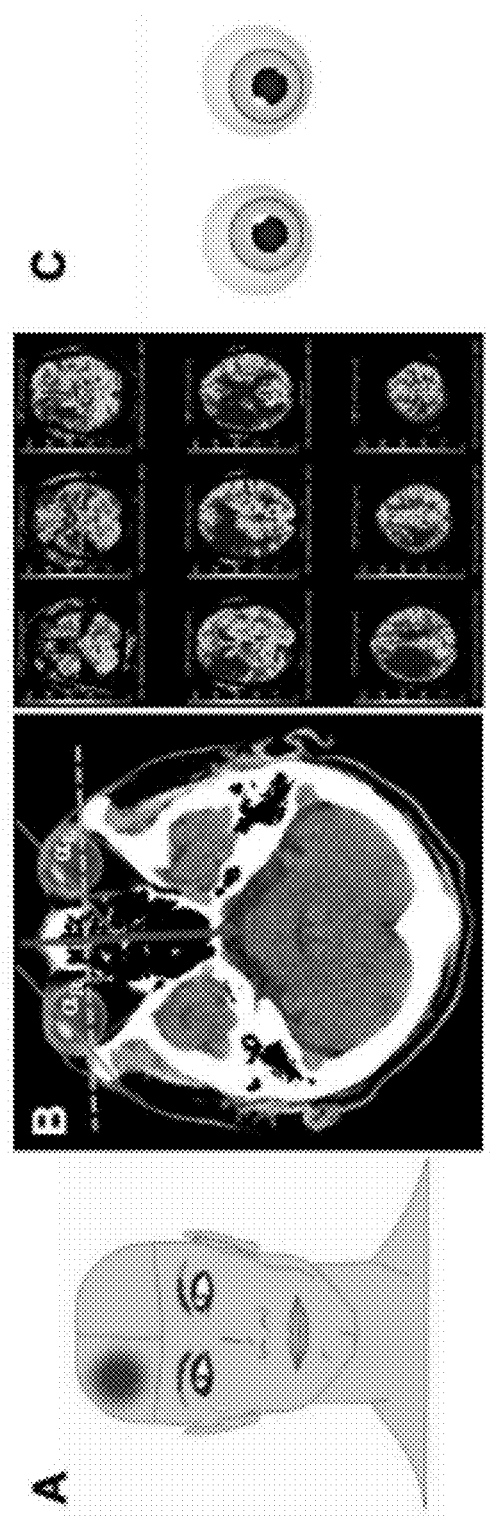
FIG. 7 includes images indicating a location of an occluded blood vessel in an individual experiencing a stroke and the correlation between gaze deviation and the location of the occluded blood vessel.

FIG. 7 includes images indicating a location of an occluded blood vessel in an individual experiencing a stroke and the correlation between gaze deviation and the location of the occluded blood vessel. Image A is a diagram showing the location of an example patient with a stroke located in the right hemisphere of the brain and having corresponding conjugate gaze deviation to the right. Image B includes a non-contrast CT image of an 80-year old patient with a distal ICA occlusion causing a large cerebral blood flow deficit in the right middle cerebral artery territory resulting in conjugate gaze deviation to the right. Gaze deviation can be determined based on the non-contrast CT data. Image C includes an example eyeball extraction by segmentation from the data of the non-contrast CT image and the corresponding location of the lenses.

Figure 8:
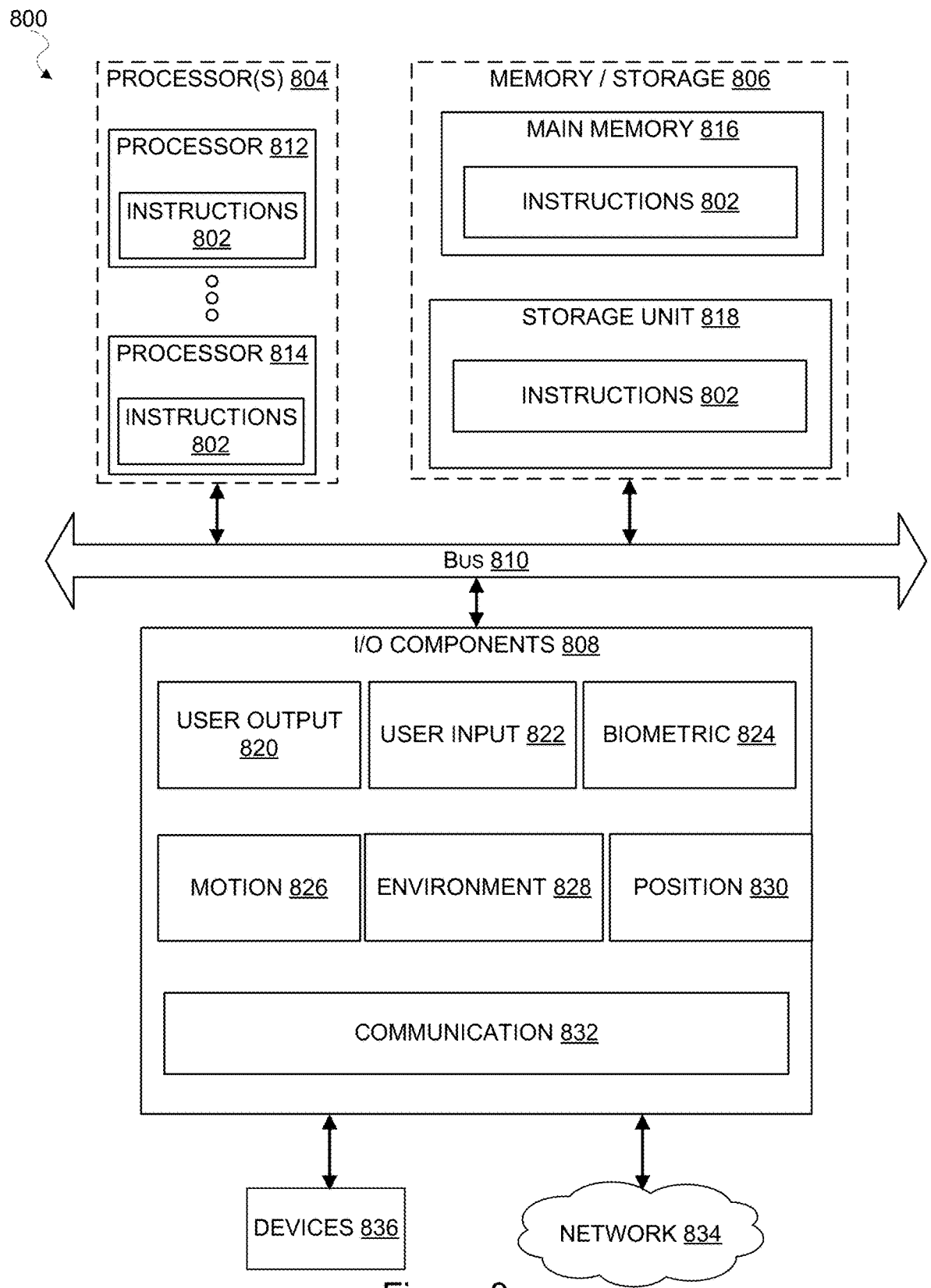
FIG. 8 is a block diagram illustrating components of a machine, in the form of a computer system, that may read and execute instructions from one or more machine-readable media to perform any one or more methodologies described herein, in accordance with one or more example implementations.

FIG. 8 is a block diagram illustrating components of a machine 800, according to some example implementations, able to read instructions from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 802 (e.g., software, a program, an application, an applet, an app, or other executable code) for causing the machine 800 to perform any one or more of the methodologies discussed herein may be executed. As such, the instructions 802 may be used to implement modules or components described herein. The instructions 802 transform the general, non-programmed machine 800 into a particular machine 800 programmed to carry out the described and illustrated functions in the manner described. In alternative implementations, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, at network switch, a network bridge, or any machine capable of executing the instructions 802, sequentially or otherwise, that specify actions to be taken by machine 800. Further, while only a single machine 800 is illustrated, the term "machine" shall also be taken to include a collection of machines that individually or jointly execute the instructions 802 to perform any one or more of the methodologies discussed herein.

The machine 800 may include processors 804, memory/storage 806, and I/O components 808, which may be configured to communicate with each other such as via a bus 810. "Processor" in this context, refers to any circuit or virtual circuit (a physical circuit emulated by logic executing on an actual processor 804) that manipulates data values according to control signals (e.g., "commands," "op codes," "machine code," etc.) and which produces corresponding output signals that are applied to operate a machine 800. In an example implementation, the processors 804 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 812 and a processor 814 that may execute the instructions 802. The term "processor" is intended to include multi-core processors 804 that may comprise two or more independent processors (sometimes referred to as "cores") that may execute instructions 802 contemporaneously. Although FIG. 8 shows multiple processors 804, the machine 800 may include a single processor 812 with a single core, a single processor 812 with multiple cores (e.g., a multi-core processor), multiple processors 812, 814 with a single core, multiple processors 812, 814 with multiple cores, or any combination thereof.

The memory/storage 806 may include memory, such as a main memory 816, or other memory storage, and a storage unit 818, both accessible to the processors 804 such as via the bus 810. The storage unit 818 and main memory 816 store the instructions 802 embodying any one or more of the methodologies or functions described herein. The instructions 802 may also reside, completely or partially, within the main memory 816, within the storage unit 818, within at least one of the processors 804 (e.g., within the processor's cache memory), or any suitable combination thereof, during execution thereof by the machine 800. Accordingly, the main memory 816, the storage unit 818, and the memory of processors 804 are examples of machine-readable media. "Machine-readable media," also referred to herein as "computer-readable storage media", in this context, refers to a component, device, or other tangible media able to store instructions 802 and data temporarily or permanently and may include, but is not limited to, random-access memory (RAM), read-only memory (ROM), buffer memory, flash memory, optical media, magnetic media, cache memory, other types of storage (e.g., erasable programmable read-only memory (EEPROM)) and/or any suitable combination thereof. The term "machine-readable medium" may be taken to include a single medium or multiple media (e.g., a centralized or distributed database, or associated caches and servers) able to store instructions 802. The term "machine-readable medium" shall also be taken to include any medium, or combination of multiple media, that is capable of storing instructions 802 (e.g., code) for execution by a machine 800, such that the instructions 802, when executed by one or more processors 804 of the machine 800, cause the machine 800 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 808 may include a wide variety of components to receive input, provide output, produce output, transmit information, exchange information, capture measurements, and so on. The specific I/O components 808 that are included in a particular machine 800 will depend on the type of machine. For example, portable machines such as mobile phones will likely include a touch input device or other such input mechanisms, while a headless server machine will likely not include such a touch input device. It will be appreciated that the I/O components 808 may include many other components that are not shown in FIG. 8. The I/O components 808 are grouped according to functionality merely for simplifying the following discussion and the grouping is in no way limiting. In various example implementations, the I/O components 808 may include user output components 820 and user input components 822. The user output components 820 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 822 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location or force of touches or touch gestures, or other tactile input components), audio input components (e.g., a microphone), and the like.

In further example implementations, the I/O components 808 may include biometric components 824, motion components 826, environmental components 828, or position components 830 among a wide array of other components. For example, the biometric components 824 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 826 may include acceleration sensor components (e.g., accelerometer), gravitation sensor components, rotation sensor components (e.g., gyroscope), and so forth. The environmental components 828 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 830 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 808 may include communication components 832 operable to couple the machine 800 to a network 834 or devices 836. For example, the communication components 832 may include a network interface component or other suitable device to interface with the network 834. In further examples, communication components 832 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 836 may be another machine 800 or any of a wide variety of peripheral devices (e.g., a peripheral device coupled via a USB).

Moreover, the communication components 832 may detect identifiers or include components operable to detect identifiers. For example, the communication components 832 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 832, such as location via Internet Protocol (IP) geo-location, location via Wi-Fi® signal triangulation, location via detecting an NFC beacon signal that may indicate a particular location, and so forth.

"Component," in this context, refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example implementations, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an ASIC. A hardware component may also include programmable logic or circuitry that is temporarily configured by software to perform certain operations. For example, a hardware component may include software executed by a general-purpose processor 804 or other programmable processor. Once configured by such software, hardware components become specific machines (or specific components of a machine 800) uniquely tailored to perform the configured functions and are no longer general-purpose processors 804. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering implementations in which hardware components are temporarily configured (e.g., programmed), each of the hardware components need not be configured or instantiated at any one instance in time. For example, where a hardware component comprises a general-purpose processor 804 processor 804 configured by software to become a special-purpose processor, the general-purpose processor 804 processor 804 may be configured as respectively different special-purpose processors (e.g., comprising different hardware components) at different times. Software accordingly configures a particular processor 812, 814 or processors 804, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In implementations in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices, and can operate on a resource (e.g., a collection of information). The various operations of example methods described herein may be performed, at least partially, by one or more processors 804 that are temporarily configured (e.g., by software) or permanently configured to perform the relevant operations. Whether temporarily or permanently configured, such processors 804 may constitute processor-implemented components that operate to perform one or more operations or functions described herein. As used herein, "processor-implemented component" refers to a hardware component implemented using one or more processors 804. Similarly, the methods described herein may be at least partially processor-implemented, with a particular processor 812, 814 or processors 804 being an example of hardware. For example, at least some of the operations of a method may be performed by one or more processors 804 or processor-implemented components. Moreover, the one or more processors 804 may also operate to support performance of the relevant operations in a "cloud computing" environment or as a "software as a service" (SaaS). For example, at least some of the operations may be performed by a group of computers (as examples of machines 800 including processors 804), with these operations being accessible via a network 834 (e.g., the Internet) and via one or more appropriate interfaces (e.g., an API). The performance of certain of the operations may be distributed among the processors, not only residing within a single machine 800, but deployed across a number of machines. In some example implementations, the processors 804 or processor-implemented components may be located in a single geographic location (e.g., within a home environment, an office environment, or a server farm). In other example implementations, the processors 804 or processor-implemented components may be distributed across a number of geographic locations.

Figure 9:
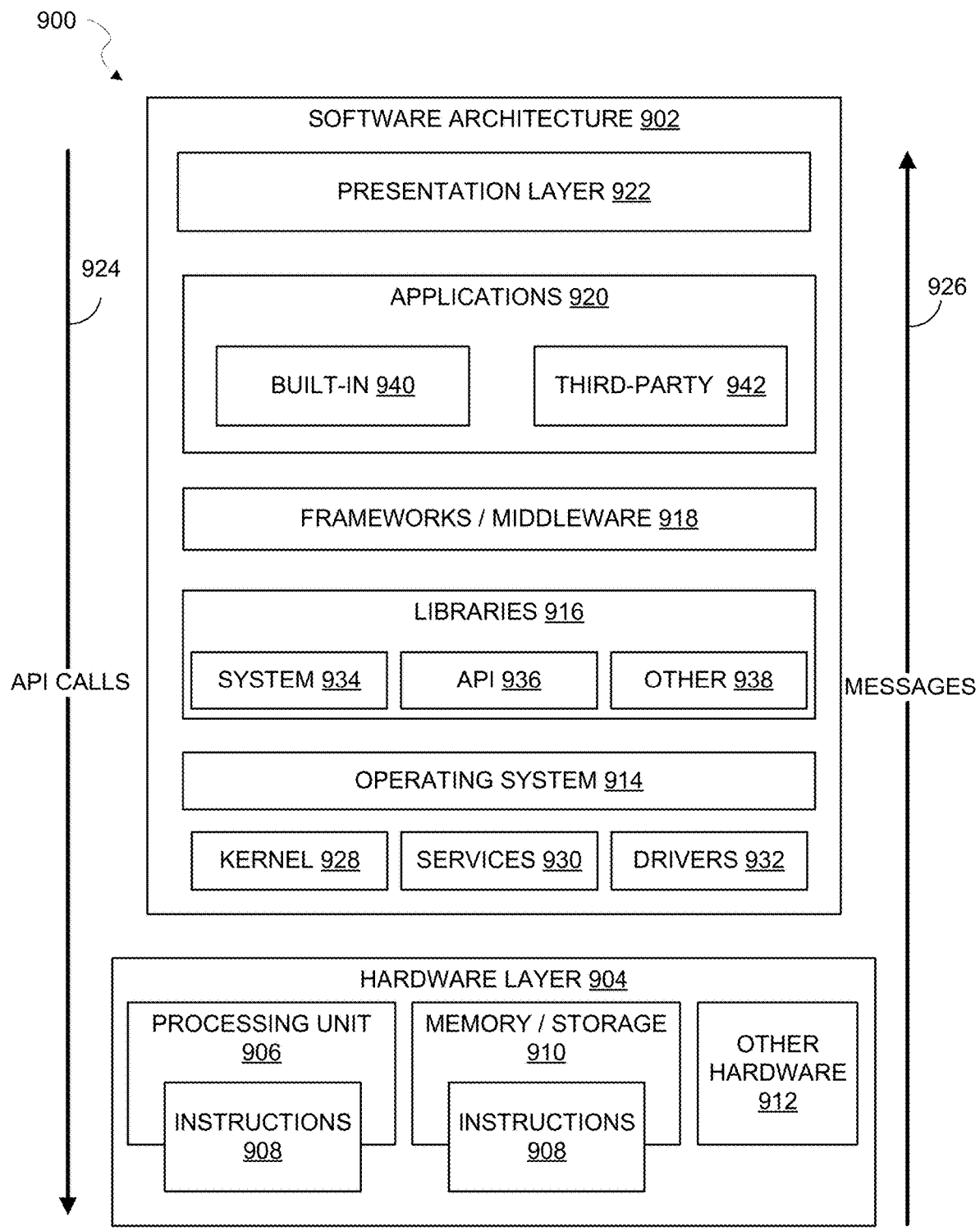
FIG. 9 is block diagram illustrating a representative software architecture that may be used in conjunction with one or more hardware architectures described herein, in accordance with one or more example implementations.

FIG. 9 is a block diagram illustrating system 900 that includes an example software architecture 902, which may be used in conjunction with various hardware architectures herein described. FIG. 9 is a non-limiting example of a software architecture and it will be appreciated that many other architectures may be implemented to facilitate the functionality described herein. The software architecture 902 may execute on hardware such as machine 800 of FIG. 8 that includes, among other things, processors 804, memory/storage 806, and input/output (I/O) components 808. A representative hardware layer 904 hardware layer 904 is illustrated and can represent, for example, the machine 800 of FIG. 8. The representative hardware layer 904 hardware layer 904 includes a processing unit 906 having associated executable instructions 908. Executable instructions 908 represent the executable instructions of the software architecture 902, including implementation of the methods, components, and so forth described herein. The hardware layer 904 also includes at least one of memory or storage modules memory/storage 910, which also have executable instructions 908. The hardware layer 904 may also comprise other hardware 912.

In the example architecture of FIG. 9, the software architecture 902 may be conceptualized as a stack of layers where each layer provides particular functionality. For example, the software architecture 902 may include layers such as an operating system 914, libraries 916, frameworks/middleware 918, applications 920, and a presentation layer 922. Operationally, the applications 920 or other components within the layers may invoke API calls 924 through the software stack and receive messages 926 in response to the API calls 924. The layers illustrated are representative in nature and not all software architectures have all layers. For example, some mobile or special purpose operating systems may not provide a frameworks/middleware 918, while others may provide such a layer. Other software architectures may include additional or different layers.

The operating system 914 may manage hardware resources and provide common services. The operating system 914 may include, for example, a kernel 928, services 930, and drivers 932. The kernel 928 may act as an abstraction layer between the hardware and the other software layers. For example, the kernel 928 may be responsible for memory management, processor management (e.g., scheduling), component management, networking, security settings, and so on. The services 930 may provide other common services for the other software layers. The drivers 932 are responsible for controlling or interfacing with the underlying hardware. For instance, the drivers 932 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 916 provide a common infrastructure that is used by at least one of the applications 920, other components, or layers. The libraries 916 provide functionality that allows other software components to perform tasks in an easier fashion than to interface directly with the underlying operating system 914 functionality (e.g., kernel 928, services 930, drivers 932). The libraries 916 may include system libraries 934 (e.g., C standard library) that may provide functions such as memory allocation functions, string manipulation functions, mathematical functions, and the like. In addition, the libraries 916 may include API libraries 936 such as media libraries (e.g., libraries to support presentation and manipulation of various media format such as MPEG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 916 may also include a wide variety of other libraries 938 to provide many other APIs to the applications 920 and other software components/modules.

The frameworks/middleware 918 (also sometimes referred to as middleware) provide a higher-level common infrastructure that may be used by the applications 920 or other software components/modules. For example, the frameworks/middleware 918 may provide various graphical user interface functions, high-level resource management, high-level location services, and so forth. The frameworks/middleware 918 may provide a broad spectrum of other APIs that may be utilized by the applications 920 or other software components/modules, some of which may be specific to a particular operating system 914 or platform.

The applications 920 include built-in applications 940 and third-party applications 942. Examples of representative built-in applications 940 may include, but are not limited to, a contacts application, a browser application, a book reader application, a location application, a media application, a messaging application, or a game application. Third-party applications 942 may include an application developed using the ANDROID™ or IOS™ software development kit (SDK) by an entity other than the vendor of the particular platform, and may be mobile software running on a mobile operating system such as IOS™, ANDROID™ WINDOWS® Phone, or other mobile operating systems. The third-party applications 942 may invoke the API calls 924 provided by the mobile operating system (such as operating system 914) to facilitate functionality described herein.

The applications 920 may use built-in operating system functions (e.g., kernel 928, services 930, drivers 932), libraries 916, and frameworks/middleware 918 to create UIs to interact with users of the system. Alternatively, or additionally, in some systems, interactions with a user may occur through a presentation layer, such as presentation layer 922. In these systems, the application/component "logic" can be separated from the aspects of the application/component that interact with a user.

Changes and modifications may be made to the disclosed implementations without departing from the scope of the present disclosure. These and other changes or modifications are intended to be included within the scope of the present disclosure, as expressed in the following claims.

What is claimed is:

1. A method comprising:
obtaining, by a computing system including one or more processing devices and one or more memory devices, imaging data from one or more imaging data sources, the imaging data corresponding to at least a portion of a face of an individual;
generating, based on the imaging data, a plurality of images of the face of the individual from a plurality of vantage points;
determining that a vantage point of an image included in the imaging data is different from a reference vantage point;
modifying a first location of a first iris of the individual and a second location of a second iris of the individual to correct for a difference between the vantage point of the image and the reference vantage point;
determining, by the computing system and based on the imaging data, a gaze deviation metric for the individual based on a first image of the plurality of images corresponding to the vantage point and a second image of the plurality of images corresponding to the reference vantage point, the gaze deviation metric indicating an offset of a location of at least one iris of the individual with respect to an expected iris location;
analyzing, by the computing system and based on the imaging data, one or more target regions of the face of the individual to determine a measure of similarity between an appearance of the one or more target regions with respect to an additional appearance of one or more additional target regions located on an opposite side of the face of the individual; determining, by the computing system and based on the measure of similarity, a facial paralysis metric of the individual, the facial paralysis metric indicating a measure of facial paralysis of the individual; analyzing, by the computing system, at least one of the gaze deviation metric or the facial paralysis metric to determine an assessment metric indicating a probability of a presence of a stroke with respect to the individual; and generating, by the computing system, user interface data corresponding to one or more user interfaces that include a user interface element indicating the probability of the presence of the stroke with respect to the individual.

2. The method of claim 1, comprising:
obtaining, by the computing system, training data that includes image training data, the image training data including:
a first set of images of first individuals that experienced a stroke that resulted in an amount of gaze deviation;
a second set of images of second individuals that experienced a stroke that resulted in an amount of facial paralysis; and
a third set of images of third individuals that did not experience a stroke, that did not have an amount of gaze deviation, and that did not have an amount of facial paralysis.

3. The method of claim 2, comprising:
analyzing, by the computing system, the second set of images and the third set of images to determine a number of regions of faces of individuals that have different characteristics between the second individuals that experienced a stroke and the first individuals that did not experience a stroke; and
identifying, by the computing system, the one or more target regions from among the number of regions.

4. The method of claim 2, comprising:
analyzing, by the computing system, the first set of images and the third set of images to determine an expected gaze that corresponds to the third individuals that did not experience a stroke; and
analyzing, by the computing system, the second set of images and the third set of images to determine an expected appearance of the one or more target regions with respect to the third individuals that did not experience a stroke.

5. The method of claim 2, wherein the training data includes classification data that labels the first set of images as being obtained from the first individuals that experienced a stroke resulting in an amount of gaze deviation, that labels the second set of images as being obtained from the second individuals that experienced a stroke resulting in an amount of facial paralysis, and that labels the third set of images as being obtained from the third individuals that did not experience a stroke.

6. The method of claim 2, comprising:
training, by the computing system and using the training data, one or more convolutional neural networks to determine the facial paralysis metric and to determine the gaze deviation metric.

7. The method of claim 6, wherein:
input to the one or more convolutional neural networks during training includes the first set of images with classification data indicating that the first individuals experienced a stroke that resulted in an amount of gaze deviation and the third set of images with additional classification data indicating that the third individuals did not have an amount of gaze deviation; and
the one or more convolutional neural networks are trained to provide output indicating a plurality of categories, individual categories of the plurality of categories corresponding to different amounts of gaze deviation.

8. The method of claim 6, wherein:
input to the one or more convolutional neural networks during training includes the second set of images with classification data indicating that the second individuals experienced a stroke that resulted in an amount of facial paralysis and the third set of images with additional classification data indicating that the third individuals did not have an amount of facial paralysis; and
the one or more convolutional neural networks are trained to provide output indicating a plurality of categories, individual categories of the plurality of categories corresponding to different amounts of facial paralysis.

9. The method of claim 1, comprising:
determining, by the computing system, a location of an occluded blood vessel of the individual based on at least one of the gaze deviation metric or the facial paralysis metric.

10. The method of claim 1, wherein the one or more imaging sources includes a computed-tomography based imaging apparatus or a magnetic resonance-based imaging apparatus.

11. The method of claim 1, wherein the one or more imaging sources includes a mobile computing device and the imaging data includes one or more images captured by the mobile computing device using a structured light pattern, using a time of flight camera, or using a LiDAR system.

12. A system comprising:
one or more hardware processors; and
one or more non-transitory computer-readable storage media including computer-readable instructions that, when executed by the one or more hardware processors, cause the one or more hardware processors to perform operations comprising:
obtaining imaging data from one or more imaging sources, the imaging data including at least a portion of a face of an individual;
generating, based on the imaging data, a plurality of images of the face of the individual from a plurality of vantage points;
determining a gaze deviation metric for the individual based on a first image of the plurality of images corresponding to a first vantage point and a second image of the plurality of images corresponding to a second vantage point, the gaze deviation metric indicating an offset of a location of at least one iris of the individual with respect to an expected iris location;
determining, based on the imaging data, a facial paralysis metric of the individual, the facial paralysis metric indicating a measure of facial paralysis of the individual;
analyzing at least one of the gaze deviation metric or the facial paralysis metric to determine an assessment metric indicating a probability of a presence of a stroke with respect to the individual; and
generating user interface data corresponding to one or more user interfaces that include a user interface element indicating the probability of the presence of the stroke with respect to the individual.

13. The system of claim 12, wherein:
the imaging data is obtained from a magnetic resonance-based imaging apparatus or a computed tomography-based imaging apparatus;
the one or more non-transitory computer-readable storage media include additional computer-readable instructions that, when executed by the one or more hardware processors, cause the one or more hardware processors to perform additional operations comprising:
generating a first additional image based on the imaging data that indicates blood vessels of the brain of the individual; and generating a second additional image based on the imaging data that includes facial features of the individual; and wherein a user interface of the one or more user interfaces includes the first additional image and the second additional image.

14. The system of claim 12, wherein:

one or more target regions include a first plurality of target regions located on a first side of the face of the individual and a second plurality of target regions located on a second side of the face of the individual, the first side of the face being contralateral with respect to the second side of the face; and the one or more non-transitory computer-readable storage media include additional computer-readable instructions that, when executed by the one or more hardware processors, cause the one or more hardware processors to perform additional operations comprising:

determining the expected appearance of the one or more target regions based on first characteristics of the first plurality of target regions; and the facial paralysis metric is determined based on differences between the first characteristics of the first plurality of target regions and second characteristics of the second plurality of target regions.

15. The system of claim 12, wherein the one or more non-transitory computer-readable storage media include additional computer-readable instructions that, when executed by the one or more hardware processors, cause the one or more hardware processors to perform additional operations comprising:

obtaining a reference image of the individual that is captured prior to a suspected incidence of a stroke occurring with respect to the individual;

determining the expected iris location based on a first location of a first iris of the individual in the reference image and a second location of a second iris of the individual in the reference image; and determining the expected appearance of the one or more target regions based on an appearance of the one or more target regions in the reference image.

16. The system of claim 12, wherein the one or more non-transitory computer-readable storage media include additional computer-readable instructions that, when executed by the one or more hardware processors, cause the one or more hardware processors to perform additional operations comprising:

determining an angular offset between a location of an iris of the individual determined based on the imaging data and the expected iris location;

wherein the gaze deviation metric is based on the angular offset.

17. The system of claim 12, wherein the one or more non-transitory computer-readable storage media include additional computer-readable instructions that, when executed by the one or more hardware processors, cause the one or more hardware processors to perform additional operations comprising:

determining the facial paralysis metric using the first image of the plurality of images corresponding to the first vantage point and the second image of the plurality of images corresponding to the second vantage point.

18. One or more non-transitory computer-readable media storing computer readable instructions that, when executed by one or more processing devices, cause the one or more processing devices to perform operations comprising:

obtaining imaging data from one or more imaging sources, the imaging data including at least a portion of a face of an individual;

determining that a vantage point of an image included in the imaging data is different from a reference vantage point;

modifying a first location of a first iris of the individual and a second location of a second iris of the individual to correct for a difference between the vantage point of the image and the reference vantage point;

determining, based on the imaging data, a gaze deviation metric for the individual according to a modified first location of the first iris and a modified location of the second iris, the gaze deviation metric indicating an offset of a location of at least one iris of the individual with respect to an expected iris location;

analyzing, based on the imaging data, one or more target regions of the face of the individual to determine a measure of similarity between an appearance of the one or more target regions with respect to at least one of an additional appearance of the one or more target regions included in a reference image or an additional appearance of one or more additional target regions located on an opposite side of the face of the individual;

determining, based on the measure of similarity, a facial paralysis metric of the individual, the facial paralysis metric indicating a measure of facial paralysis of the individual;

analyzing at least one of the gaze deviation metric or the facial paralysis metric to determine an assessment metric indicating a probability of a presence of a stroke with respect to the individual; and generating user interface data corresponding to one or more user interfaces that include a user interface element indicating the probability of the presence of the stroke with respect to the individual.

19. The one or more non-transitory computer-readable media of claim 18, storing additional computer-readable instructions that, when executed by the one or more processing devices, cause the one or more processing devices to perform additional operations comprising:

determining a binary mask that indicates first portions of the imaging data that correspond to a foreground and second portions of the imaging data that correspond a background;

generating a mesh of polygons that correspond to a surface of the face of the individual; and rendering the mesh of polygons to generate an image of the face of the individual.

20. The one or more non-transitory computer-readable media of claim 18, storing additional computer-readable instructions that, when executed by the one or more processing devices, cause the one or more processing devices to perform additional operations comprising:

performing one or more segmentation processes with respect to the imaging data to identify eyes of the individual.

* * * * *